United States Patent [19]
Beck et al.

[11] Patent Number: 5,625,104
[45] Date of Patent: Apr. 29, 1997

[54] ALKALI METAL ION EXCHANGED SELECTIVATED ZEOLITE CATALYST

[75] Inventors: Jeffrey S. Beck, Princeton; David L. Stern, Lawrenceville, both of N.J.

[73] Assignee: Mobil Oil Corporation, Fairfax, Va.

[21] Appl. No.: 471,631

[22] Filed: Jun. 6, 1995

[51] Int. Cl.$^6$ .................................................. C07C 5/22
[52] U.S. Cl. ..................... 585/475; 585/533; 585/481; 208/27
[58] Field of Search ................... 585/475, 481, 585/533, 407; 208/111, 86, 257, 418, 27

[56] References Cited

U.S. PATENT DOCUMENTS

| | | |
|---|---|---|
| 3,251,897 | 5/1966 | Wise . |
| 3,257,310 | 6/1966 | Plank et al. . |
| 3,437,587 | 4/1969 | Elbert et al. . |
| 3,682,996 | 8/1972 | Kerr . |
| 3,698,157 | 10/1972 | Allen et al. . |
| 4,016,218 | 4/1977 | Haag et al. . |
| 4,049,738 | 9/1977 | Young . |
| 4,060,568 | 11/1977 | Rodewald . |
| 4,086,287 | 4/1978 | Kaeding et al. . |
| 4,090,981 | 5/1978 | Rodewald . |
| 4,100,215 | 7/1978 | Chen . |
| 4,117,024 | 9/1978 | Kaeding . |
| 4,127,616 | 11/1978 | Rodewald . |
| 4,145,315 | 3/1979 | Rodewald . |
| 4,224,141 | 9/1980 | Morrison et al. . |
| 4,283,306 | 8/1981 | Herkes . |
| 4,326,994 | 4/1982 | Haag et al. . |
| 4,390,414 | 6/1983 | Cody . |
| 4,402,867 | 9/1983 | Rodewald . |
| 4,443,554 | 4/1984 | Dessau . |
| 4,465,886 | 8/1984 | Rodewald . |
| 4,477,583 | 10/1984 | Rodewald . |
| 4,487,843 | 12/1984 | Telford et al. . |
| 4,522,929 | 6/1985 | Chester et al. . |
| 4,548,914 | 10/1985 | Chu . |
| 4,559,314 | 12/1985 | Shihabi . |
| 4,843,057 | 6/1989 | D'Amore et al. . |
| 4,851,604 | 7/1989 | Absil et al. . |
| 4,927,979 | 5/1990 | Yamagishi et al. . | |
| 4,950,835 | 8/1990 | Wang et al. . | |
| 5,173,461 | 12/1992 | Absil et al. . | |
| 5,321,183 | 6/1994 | Chang et al. | 585/475 |
| 5,349,113 | 9/1994 | Chang et al. | 585/475 |
| 5,349,114 | 9/1994 | Lago et al. | 585/475 |
| 5,365,003 | 11/1994 | Chang et al. | 585/470 |
| 5,365,004 | 11/1994 | Beck et al. | 585/475 |
| 5,367,099 | 11/1994 | Beck et al. | 585/475 |
| 5,382,737 | 1/1995 | Beck et al. | 585/475 |
| 5,403,800 | 4/1995 | Beck et al. | 502/64 |
| 5,406,015 | 4/1995 | Beck et al. | 585/475 |
| 5,455,213 | 10/1995 | Chang et al. | 502/63 |
| 5,475,179 | 12/1995 | Chang et al. | 585/475 |
| 5,476,823 | 12/1995 | Beck et al. | 502/60 |
| 5,488,194 | 1/1996 | Beck et al. | 585/475 |
| 5,495,059 | 2/1996 | Beck et al. | 585/470 |
| 5,498,814 | 3/1996 | Chang et al. | 585/475 |
| 5,516,736 | 5/1996 | Chang et al. | 585/475 |
| 5,516,956 | 5/1996 | Abchandani et al. | 585/481 |

FOREIGN PATENT DOCUMENTS

0296582A2  6/1988  European Pat. Off. .

OTHER PUBLICATIONS

Nakajima et al., "p–Xylene–Selective Disproportionation of Toluene over a Modified Pentasil Type Zeolite", *Sekiyu Gakkaishi*, 35(2), 185–189 (1992).

Hibino et al., "Shape–Selectivity over HZSM–5 Modified by Chemical Vapor Deposition of Silicon Alkoxide", *Journal of Catalysis*, 128, 551–558 (1991).

Lago et al., "The Nature of the Catalytic Sites in HZSM–5 Activity Enhancement", *New Development in Zeolite Science Technology: Proceeding of the 7th International Zeolite Conference*, 677–684 (1986).

Primary Examiner—Steven Bos
Assistant Examiner—Thomas G. Dunn, Jr.
Attorney, Agent, or Firm—P. W. Roberts; M. D. Keen

[57] ABSTRACT

There is provided a zeolite catalyst, which is first selectivated with a siliceous material and then treated with an aqueous solution comprising alkali metal ions under ion exchange conditions.

3 Claims, No Drawings

ALKALI METAL ION EXCHANGED SELECTIVATED ZEOLITE CATALYST

BACKGROUND

There is provided a zeolite catalyst, which is first selectivated with a siliceous material and then treated with an aqueous solution comprising alkali metal ions under ion exchange conditions.

Shape-selective catalysis is described, e.g., by N. Y. Chen, W. E. Garwood, and F. G. Dwyer, *Shape Selective Catalysis in Industrial Applications*, 36, Marcel Dekker, Inc. (1989). Within a zeolite pore, hydrocarbon conversion reactions such as isomerization, disproportionation, alkylation, and transalkylation of aromatics are governed by constraints imposed by the channel size. Reactant selectivity may occur when a fraction of the feedstock is too large to enter the zeolite pores to react, while product selectivity may occur when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape-selective catalysis is demonstrated, for example, in selective alkyl-substituted benzene disproportionation to para-dialkyl-substituted benzene.

A representative para-dialkyl-substituted benzene is para-xylene. The production of para-xylene may be performed by methylation of toluene or by toluene disproportionation over a catalyst under conversion conditions. Examples include the reaction of toluene with methanol, as described by Chen et al., *J. Amer. Chem. Soc.*, 101, 6783 (1979), and toluene disproportionation, as described by Pines in *The Chemistry of Catalytic Hydrocarbon Conversions*, Academic Press, 72 (1981). Such methods may result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Various methods are known in the art for increasing the para-selectivity of zeolite catalysts. One such method is to modify the catalyst by treatment with a "selectivating agent." For example, U.S. Pat. No. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

U.S. Pat. No. 4,283,306 to Herkes discloses the promotion of crystalline silica catalyst by application of an amorphous silica such as ethylorthosilicate (i.e., tetraethylorthosilicate). The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that the multiple ex situ selectivation confers no benefit and in fact reduces a catalyst's efficacy in shape-selective reactions.

Steaming has also been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation.

SUMMARY

There is provided a method for preparing a selectivated catalyst composition, said method comprising the steps of:

(a) contacting a catalyst comprising a zeolite with an organosilicon compound under conditions sufficient to deposit a siliceous material on said catalyst;

(b) contacting the catalyst comprising a zeolite and siliceous material from step (a) with an aqueous solution comprising at least one alkali metal cation;

(c) washing the aqueous solution treated catalyst from step (b) with water;

(d) drying the washed catalyst from step (c); and (e) recovering a catalyst composition comprising said zeolite, said siliceous material and alkali metal ions from said aqueous solution of step (b). Optionally, steps (b) and (c) may be repeated at least once before conducting step (d). Also, the dried, ion-exchanged catalyst may, optionally, be calcined, e.g., in pure nitrogen or air at a temperature from 200° F. to 1200° F., e.g., from 500° F. to 1000° F.

There is also provided a process for hydrocarbon conversion, said process comprising contacting a reaction stream comprising hydrocarbon to be converted, under conversion conditions, with a catalyst prepared by the above-mentioned selectivation/ion exchange method.

EMBODIMENTS

The present catalyst may comprise at least 0.03 wt.%, e.g., at least 0.1 wt.%, of alkali metal. Particular alkali metals include Li, Na, K, Rb, and Cs.

The present alkali metal ion exchange procedure may be used to decrease the activity of the catalyst. Certain reactions such as toluene disproportionation tend to require high activity catalysts. However, other reactions, such as alkylation of toluene or ethylbenzene with ethylene, require less active catalysts, e.g., to avoid undesired side reactions. Accordingly, the present ion exchange procedure provides a means to tailor the activity of the basic selectivated catalyst. The activity may be adjusted on a small scale to fine-tune batches of the catalyst for a particular use or the activity may be adjusted on a major scale to convert the catalyst from one type to another, thereby providing a means to manufacture different catalysts for different uses.

Sources of lithium ions include lithium acetate, lithium acetylsalicylate, lithium carbonate, lithium chlorate, lithium perchlorate, lithium chloride, lithium bromide, lithium fluoride, lithium iodide, lithium iodate, lithium nitrite, lithium nitrate, lithium oxalate, lithium palmitate, lithium salicylate, lithium sulfate, lithium tartarate, lithium sulfide, lithium thiocyanate, lithium phosphate, lithium ammonium phosphate, lithium hydroxide, lithium cyanide, and lithium stearate.

Sources of sodium ions include sodium acetate, sodium barbital, sodium benzoate, sodium carbonate, sodium chloride, sodium chlorate, sodium bromide, sodium bromate, sodium perchlorate, sodium chlorite, sodium hypochlorite, sodium cinnamate, sodium citrate, sodium cyanate, sodium cyanide, sodium ethylacetoacetate, sodium hydride, sodium hydrogen fluoride, sodium formate, sodium glutamate, sodium iodide, sodium iodate, sodium periodate, sodium hydroxide, sodium lactate, sodium methoxide, sodium ethoxide, sodium nitrate, sodium nitrite, sodium oleate, sodium oxalate, sodium palmitate, sodium phenoxide, sodium carbonate, sodium bicarbonate, sodium propionate, sodium salicylate, sodium stearate, sodium succinate, sodium sulfate, sodium persulfate, sodium hydrogen sulfate, sodium hydrogen sulfide, sodium sulfide, sodium sulfite, sodium tartarate, sodium thiocyanate, sodium thiosulfate, and sodium ammonium tartarate.

Sources of potassium ions include potassium acetate, potassium acetyl salicylate, potassium bromide, potassium bromate, potassium chloride, potassium camphorate, potassium carbonate, potassium chloride, potassium chlorate, potassium perchlorate, potassium hypochlorite, potassium chloroiodate, potassium citrate, potassium cyanate, potassium cyanide, potassium ethylsulfate, potassium hydride, potassium fluoride, potassium hydroxide, potassium iodate, potassium iodide, potassium lactate, potassium laurate, potassium malate, potassium methylsulfate, potassium nitrate, potassium nitrite, potassium oleate, potassium oxalate, potassium picrate, potassium phthalate, potassium piperate, potassium sorbate, potassium stearate, potassium sulfate, potassium succinate, potassium pyrosulfate, potassium sulfide, potassium hydrogen sulfide, potassium sulfite, potassium tartarate, potassium thiocyanate, potassium dithionate, and potassium xanthate.

Sources of cesium ions include cesium acetate, cesium benzoate, cesium bromide, cesium bromate, decium carbonate, cesium hydrogen carbonate, cesium chloride, cesium chlorate, cesium perchlorate, cesium fluoride, cesium formate, cesium hydride, cesium hydroxide, cesium iodide, cesium iodate, cesium periodate, cesium nitrate, cesium nitrite, cesium oxalate, cesium oxide, cesium salicylate, cesium sulfate, cesium sulfide, cesium tartarate, and cesium hydrogen tartarate.

The parent zeolite, which is subjected to the selectivation treatment described herein, is preferably an intermediate pore size zeolite. Such intermediate pore size zeolites may have a Constraint Index of between about 1 and 12. A method for determining Constraint Index is described in U.S. Pat. No. 4,016,218. Examples of zeolites which have a Constraint Index from about 1 to 12 include ZSM-5, ZSM-11, ZSM-12, ZSM-22, ZSM-23, ZSM-35, ZSM-48, ZSM-50 and ZSM-57. An especially preferred zeolite is ZSM-5. Such zeolites are described, for example, in U.S. Pat. Nos. 3,702, 886; Re. 29,949; 3,709,979; 3,832,449; 4,046,859; 4,556, 447; 4,076,842; 4,016,245; 4,397,827; 4,640,849; 4,046, 685; 4,175,114; 4,199,556; 4,341,7448; 3,308,069; and U.S. Pat. No. Re. No. 28,341.

Zeolites, such as ZSM-5, may be selectivated with a siliceous material by a vapor phase process or a liquid phase process. An example of a liquid phase selectivation process is described herein as a preselectivation or ex situ selectivation process. The preselectivation treatment involves depositing siliceous material on the catalyst by the steps of:

(a) combining a zeolite with an organosilicon compound; and (b) calcining the organosilicon containing material in an oxygen containing atmosphere under conditions sufficient to remove organic material therefrom and leave the siliceous material on the zeolite.

Examples of preselectivation techniques are provided in copending U.S. application Ser. Nos. 08/069,251; 08/069, 254; 08/069,255; and 08/069,259, each filed May 28, 1993. Ser. No. 08/069,254 is now U.S. Pat. No. 5,367,099; Ser. No. 08/069,255 is now U.S. Pat. No. 5,404,800; and Ser. No. 08/069,259 is now U.S. Pat. No. 5,365,004. Ser. No. 08/069, 251 is now U.S. Pat. No. 5,476,823.

The preselectivation treatment may result in the deposition of at least 1 wt % of siliceous material on the catalyst.

A zeolite may be combined with a binder material for the zeolite. This binder material is preferably an inert, non-alumina binder material, such as a silica binder. A zeolite may be subjected to one or more selectivation treatments after the zeolite is combined with the binder material. Optionally, however, the zeolite may be selectivated in the unbound state.

Procedures for preparing silica bound zeolites, such as ZSM-5, are described in U.S. Pat. Nos. 4,582,815; 5,053, 374; and 5,182,242. A particular procedure for binding ZSM-5 with a silica binder involves an extrusion process.

A particular process for preparing a silica-bound zeolite may comprise the steps of:

(a) mulling and then extruding a mixture comprising water, zeolite, colloidal silica and sodium ions under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said zeolite with ammonium cations; and (c) calcining the ammonium exchanged extrudate of step (b) under conditions sufficient to generate the hydrogen form of said zeolite and increase the crush strength of said extrudate.

In accordance with examples of a preselectivation technique, the catalyst may be preselectivated by single or multiple treatments with a liquid organosilicon compound in a liquid carrier, each treatment being followed by calcination of the treated material in an oxygen containing atmosphere, e.g., air.

In accordance with the multiple impregnation preselectivation method, the zeolite is treated at least twice, e.g., from 2 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. Stable aqueous emulsions of organosilicon compounds (e.g., silicone oil) are described in copending U.S. application Ser. No. 8/141,758, filed Oct. 27, 1993 now abandoned. These emulsions are generated by mixing the organosilicon oil and an aqueous component in the presence of a surfactant or surfactant mixture. Useful surfactants include any of a large variety of surfactants, including ionic and non-ionic surfactants. Preferred surfactants include non-nitrogenous non-ionic surfactants such as alcohol, alkylphenol, and polyalkoxyalkanol derivatives, glycerol esters, polyoxyethylene esters, anhydrosorbitol esters, ethoxylated anhydrosorbitol esters, natural fats, oils, waxes and ethoxylated esters thereof, glycol esters, polyalkylene oxide block copolymer surfactants, poly(oxyethylene-co-oxypropylene) non-ionic surfactants, and mixtures thereof. More preferred surfactants include surfactants having the formula $\alpha$-[4-(1,1,3,3-tetramethylbutyl)phenyl]-$\omega$-hydroxypoly(oxy-1,2-ethanediyl) (Octoxynols), most preferably octoxynol-9. Such preferred surfactants include the TRITON® X series, such as TRITON® X-100 and TRITON® X-305, available from Rohm & Haas Co., Philadelphia, Pa. and the Igepal CA series from GAF Corp., New York, N.Y. Emulsions formulated using such surfactants are effective for selectivating ZSM-5 to enhance shape selectivity, and to passivate surface acidity detrimental to product selectivity in certain regioselective catalytic applications such as the disproportionation of alkylbenzenes.

The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetra-siloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenylmethyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as —N(CH$_3$)$_3$, —N(C$_2$H$_5$)$_3$ and —N(C$_3$H$_7$)$_3$. A preferred water soluble organosilicon preselectivating agent is an n-propylamine silane, available as Hydrosil 2627 from Huls America.

When the zeolite is preselectivated by a single or multiple impregnation technique, the zeolite is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200° C., but below the temperature at which the crystallinity of the zeolite is adversely affected. This calcination temperature may be below 700° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., N$_2$, atmosphere. An example of an oxidizing atmosphere is an oxygen containing atmosphere, such as air. Calcination may take place initially in an inert, e.g., N$_2$, atmosphere, followed by calcination in an oxygen containing atmosphere, such as air or a mixture of air and N$_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and duration of the calcination.

Preferably, the kinetic diameter of both the organosilicon compound, which is used to preselectivate the zeolite, and the organosilicon compound (e.g., silicone compound), which is used to functionalize the zeolite, is larger than the zeolite pore diameter, in order to avoid entry of the organosilicon compound into the zeolite pores and any concomitant reduction in the internal activity of the zeolite.

Vapor phase processes for selectivating zeolites are described in copending U.S. application Ser. Nos. 08/223, 383, filed Feb. 25, 1993 now U.S. Pat. No. 5,498,814; 08/233,542, filed May 5, 1994 now U.S. Pat. No. 5,475,179; 08/306,567, filed Sep. 15, 1994 now U.S. Pat. No. 5,571,768; and Ser. No. 08/306,566, filed Sep. 15, 1994 now U.S. Pat. No. 5,516,736.

The organosilicon compound which is used to vapor phase selectivate the zeolite may be a silicone or a silane. Silicones are defined herein as those compounds wherein silicon atoms are bonded to one another via oxygen atoms. Silanes are defined herein as those compounds wherein silicon atoms are bonded directly to one another.

The silicone compound which may be used to vapor phase selectivate the present zeolite may be considered to be constructed of a siloxy backbone structure capped with terminal groups. This siloxy backbone structure may be a chain structure represented by the formula

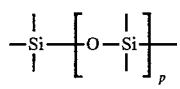

where p is from 1 to 9. This siloxy backbone structure may also be a cyclic structure represented by the formula

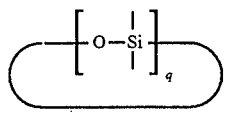

where q is from 2 to 10. Branched chain structures and composite chain/cyclic structures are also possible for the siloxy backbone of the silicone selectivating agent.

The hydrocarbyl groups which cap the available bonds of the siloxy backbone may have from 1 to 10 carbon atoms. Examples of such hydrocarbyl groups are methyl and phenyl.

Examples of silicone compounds, useful as vapor phase selectivating agents, having a chain siloxy backbone structure include those of the formula

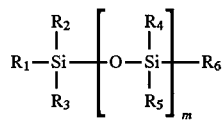

where $R_1$ and $R_6$ are independently hydrogen, methyl, or phenyl; $R_2$, $R_3$, $R_4$, and $R_5$ are independently methyl or phenyl; and m is from 1 to 10, e.g., from 1 to 4. Preferably, no more than one phenyl group is bonded to each silicon atom. Particular examples of such silicone compounds having a chain siloxy backbone structure include hexamethyldisiloxane, decamethyltetrasiloxane and diphenyltetramethyldisiloxane. Particular examples of silicone compounds having a cyclic siloxy backbone structure include octamethylcyclotetra-siloxane and decamethylcyclopentasiloxane. Particular examples of silicone compounds having a branched siloxy backbone structure are tris-(trimethylsiloxy)-phenylsilane and tris-(trimethylsiloxy)-silane.

The silane compounds, useful as vapor phase selectivating agents, may have structures corresponding to the above-mentioned silicone compounds, wherein the silicon atoms are bonded directly to one another instead of via oxygen atoms. Examples of silanes having a chain backbone structure include those of the formula

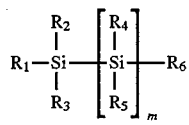

where $R_1$ and $R_6$ are independently hydrogen, methyl, or phenyl; $R_2$, $R_3$, $R_4$, and $R_5$ are independently methyl or phenyl; and m is from 1 to 10, e.g., from 1 to 4. An example of such a silane compound is hexamethyldisilane.

The vapor phase treatment is believed to result in the generation of functionalized zeolites, thereby serving to selectivate the zeolite for catalyzing certain reactions such as the disproportionation of toluene. Accordingly, the present vapor phase selectivation treatment is also referred to herein as a functionalization treatment.

The present zeolite may be selectivated by more than one selectivation method, including those which are distinguished from the present selectivation method. In particular, prior to contact with the present vapor phase silicone functionalizing agent, the zeolite may be contacted with a liquid phase including an organosilicon compound, followed by calcination in an oxygen containing atmosphere. Such a pretreatment of the zeolite is referred to herein as a preselectivation treatment.

In accordance with the present vapor phase selectivation or functionalization method described herein, the zeolite is contacted with a feed stream comprising a silicone or silane compound under vapor phase conditions. The silicone or silane compound may be applied to the zeolite neat (i.e., in the absence of a carrier or other cofeed) by a chemical vapor deposition technique. This feed stream may also comprise hydrogen and/or an organic carrier. Vapor phase conditions may include a temperature ranging from about 100° C. to about 600° C., e.g., from about 300° C. to about 500° C. When the silicone or silane compound is applied neat, reduced pressures, e.g., from about 0.5 Torr to less than atmospheric, may be used. Preferably, however, the silicone or silane compound is applied along with cofed hydrogen (i.e., $H_2$) and an organic carrier. In general, vapor phase conditions may include a pressure ranging from about 0 to about 2000 psig, e.g., from about 15 to about 800 psig, a mole ratio of hydrogen to hydrocarbons (e.g., toluene) from about 0.1 to 20, e.g., from about 0.1 to 10, e.g., from about 1 to about 4, and a weight hourly space velocity (WHSV) from about 0.1 to about 100 $hr^{-1}$, from about 0.1 to about 10 $hr^{-1}$. The organic carrier may be a hydrocarbon, especially an aromatic hydrocarbon such as toluene, benzene, xylenes and trimethylbenzenes. Toluene may comprise about 50 wt% to 100 wt%, e.g., at least 80 wt%, of the hydrocarbons in the feedstock.

When a reactive hydrocarbon, such as toluene is included in the feedstock, the presence of a sufficient amount of hydrogen in the selectivation feedstock is necessary to prevent rapid aging of the catalyst during the selectivation process resulting in an excessive reduction in the zeolite activity, possibly accompanied by a reduction in toluene disproportionation selectivity to para-xylene. This rapid aging is believed to result from a rapid build-up of excessive amounts of carbonaceous deposits (i.e., coke), which may even extend into the pore system of the zeolite in the catalyst. However, even when hydrogen is used in optimal fashion to prevent aging during the selectivation process, a small amount of carbonaceous deposit may form on the catalyst. The presence of hydrogen may also serve to induce or enhance the chemical reaction between the zeolite and the selectivating agent, which results in the functionalization of the zeolite. This chemical reaction is also believed to be induced or enhanced by elevated contact temperatures, which may be needed to maintain the silicone or silane functionalizing agent in the vapor phase.

Confirmation of the reaction between the zeolite and the silicone or silane compound may be made by an appropriate analysis of the zeolite after the reaction, as well as by monitoring and analyzing the off-gases produced by the reaction. Analysis of the zeolite will indicate the presence of hydrocarbyl groups incorporated onto the zeolite from the organosilicon selectivating agent. When the functionalized zeolite is used as a catalyst in an organic conversion process, these hydrocarbyl groups may remain intact on the zeolite. More particularly, one may intentionally avoid the customary practice of precalcining the zeolite, prior to the organic conversion process, under conditions sufficient to decompose and/or burn off organic residue on the catalyst. Such precalcination conditions to be avoided may include contact of the zeolite at temperatures greater than 300° C. in an oxygen-containing atmosphere, e.g., air.

Selectivation of the zeolite may occur, in-situ, during the course of an organic conversion reaction catalyzed by the zeolite, by including an organosilicon selectivating agent, optionally along with $H_2$, in the feed to the organic conversion reaction. This type of in-situ selectivation is also referred to herein as trim selectivation.

The selectivated zeolite is a catalyst. This catalyst may be used alone or in combination with other catalyst components included in catalysts of this type. Such other components include binders and hydrogenation/dehydrogenation components. Accordingly, it will be understood that the term, present catalyst, as used herein is intended to connote the presently selectivated zeolite in combination with other catalyst components, if any.

While not wishing to be bound by any theory, it is theorized that the extreme selectivity of the present catalyst is obtained by rendering acid sites on the external surfaces of the zeolite substantially inaccessible to reactants, while possibly increasing the tortuosity of the catalyst pore system. In a toluene disproportionation process using a non-selectivated catalyst, acid sites existing on the external surfaces of the zeolite are believed to isomerize the product para-xylene back to an equilibrium level with the other two xylene isomers, thereby reducing the amount of para-xylene in the xylenes to only about 24%. By reducing the availability of these external acid sites to the product para-xylene, it is theorized that a relatively high proportion of the para isomer can be retained. It is theorized that external zeolite acid sites are blocked or otherwise unavailable to para-xylene in the present catalyst. The extreme para-selectivity of the present catalyst is especially surprising in the highly active forms of the catalyst.

The "alpha value" of a catalyst is an approximate indication of its catalytic cracking activity. The alpha test is described in U.S. Pat. No. 3,354,078 and in the *Journal of Catalysis*, Vol. 4, 522–529 (1965); Vol. 6, 278 (1966); and Vol. 61, 395 (1980), each incorporated herein by reference to that description. It is noted that intrinsic rate constants for many acid-catalyzed reactions are proportional to the alpha value for a particular crystalline silicate catalyst (see "The Active Site of Acidic Aluminosilicate Catalysts," *Nature*, Vol. 309, No. 5959, 589–591, (1984)). The experimental conditions of the alpha test preferably include a constant temperature of 538° C. and a variable flow rate as described in detail in the *Journal of Catalysis*, Vol. 61, 395 (1980). The present catalysts, prior to alkali metal exchange, may have an alpha value greater than 50, e.g., greater than 200, e.g., from about 200 to about 1500. The alpha value of the catalyst may be increased by mild steaming before selectivation. This type of steaming is discussed in U.S. Pat. No. 4,326,994.

As mentioned previously, the present alkali metal exchange procedure may result in a decrease in the activity of the catalyst. When only a small amount of alkali metal ions is incorporated into the catalyst, e.g., in accordance with an effort to fine-tune the activity of the catalyst, the alpha value of the catalyst may be reduced by a small amount, e.g., by 10% or less. However, when a larger amount of alkali metal ions is exchanged onto the catalyst, e.g., in an effort to produce a low activity catalyst, the alpha value of the catalyst may be reduced by a larger amount, e.g., by at least 50%, e.g., at least 90%.

The silica to alumina ratio of zeolites may be determined by conventional analysis. This ratio is meant to represent, as closely as possible, the ratio in the rigid atomic framework of the zeolite crystal and to exclude silicon or aluminum in the binder or in cationic or other form within the channels. The silica to alumina molar ratio of the ZSM-5 used to prepare the present catalysts may be, e.g., less than 200, e.g., less than 100, e.g., less than 60, e.g., less than 40, e.g., from about 20 to about 40. It will be appreciated that it may be extremely difficult to directly measure the silica to alumina ratio of zeolite after it has been combined with a binder material and selectivated by methods described hereinabove. Accordingly, the silica to alumina ratio has been expressed hereinabove in terms of the silica to alumina ratio of the parent zeolite, i.e., the zeolite used to prepare the catalyst, as measured prior to the selectivation of the zeolite and prior to the combination of this zeolite with the other catalyst components.

The crystal size of the parent zeolites of the present catalysts is preferably greater than 0.1 microns, as calculated by methods described hereinbelow. The accurate direct measurement of the crystal size of zeolite materials is frequently very difficult. Microscopy methods, such as SEM and TEM, may be used, but these methods require measurements of a large number of crystals and, for each crystal measured, values may be evaluated in up to three dimensions. Furthermore, in order to more completely characterize the crystal size of a batch of crystals, one should calculate the average crystal size, as well as the degree of variance from this average in terms of a crystal size distribution. Rather than relying upon such complex evaluations, crystal size is expressed herein in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, *The Mathematics of Diffusion*, Clarendon Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% capacity of hydrocarbon, is:

$$d = 0.0704 \times t_{0.3}^{1/2}.$$

Particular measurements expressed herein were made on a computer controlled, thermogravimetric electrobalance, but there are numerous ways one skilled in the art could obtain the data. Examples of larger crystal material have a sorption time, $t_{0.3}$, of 497 minutes, which gives a calculated crystal size of 1.6 microns. Examples of smaller crystal material have a sorption time of 7.8 minutes, and a calculated size of 0.20 microns.

As pointed out in the aforementioned U.S. Pat. No. 4,117,026, larger crystal size zeolites tend to have a greater intrinsic para-selectivity than smaller crystal size zeolites. It is theorized that this difference is attributable to the smaller ratio of external surface area to available internal surface area for larger zeolites as compared to smaller crystal size zeolites. Since it would theoretically require less selectivation to neutralize the external surface area of the more intrinsically para-selective larger crystal size zeolites, larger crystal size zeolites would be preferred to smaller crystal size zeolites, provided that all other factors were equal. However, there are other factors which tend to mitigate against a preference for larger crystal size zeolites, particularly ZSM-5. More particularly, larger crystal size ZSM-5 having a high activity and corresponding low silica to alumina molar ratio, e.g., from about 20 to about 40, is considerably more difficult to prepare than smaller crystal size ZSM-5, especially on a commercial scale. A particularly surprising aspect of the present siliceous material selectivated catalysts is that the zeolites thereof may comprise relatively small crystal size ZSM-5, e.g., having a crystal size of from about 0.1 to about 0.5 microns and a silica to alumina molar ratio of from about 20 to 40, and still have an extremely high degree of para-selectivity. When larger crystal size ZSM-5 is chosen for the present catalyst, this the crystal size of this ZSM-5 may be, for example, from about 1 to 2 microns.

The present catalyst may be used for the production of para-xylene via the catalytic disproportionation of toluene. More particularly, this catalyst, under disproportionation conditions, is capable of producing a very high proportion of para-xylene among the total of the xylene isomers. However, it will be understood that this catalyst may also be used to catalyze other organic, especially hydrocarbon, conversion reactions.

When the present catalyst is used in a toluene disproportionation reaction, the reaction conditions may include a temperature of about 350° C. –540° C., a pressure of about atmospheric—5000 psig, a toluene feed rate of about 0.1–20 WHSV, and a hydrogen to toluene mole ratio of about 0.1–20. The hydrogen cofeed serves to suppress catalyst aging, thereby dramatically increasing the cycle length.

The liquid feedstock for the present toluene disproportionation reaction may, optionally, include hydrocarbons other than toluene. Such hydrocarbons include non-aromatic hydrocarbons, such as paraffins and/or cycloparaffins. These non-aromatics may have boiling points close to the boiling point of toluene, which is about 111° C. These non-aromatics are, therefore, difficult to remove from toluene by distillation, and extraction techniques may be needed to separate these toluene coboilers from toluene. The amount of non-aromatics in the fresh feed may be from 0 wt.% to about 3 wt.%, e.g., from about 0.2 wt.% to about 1.5 wt.%. It will also be understood that commercial toluene disproportionation reactions are run by recycling unconverted toluene. The amount of recycled toluene in the feed to the reactor will vary on the amount of toluene conversion per pass. For example, this feed may comprise from about 50 wt.% to about 85 wt.% of recycled toluene. As a result, difficult to remove non-aromatic constituents (e.g., toluene coboilers) may build up in the recycle stream. These toluene coboilers may eventually comprise from about 2 wt.% to about 15 wt.% of the toluene recycle stream. Thus, the total liquid feed to the present disproportionation reactor may comprise both fresh (i.e., make-up) toluene and recycled toluene, and this liquid feed may comprise from 0 wt.% to about 15 wt.% of non-aromatics.

When the present catalyst is used in an ethylbenzene disproportionation reaction, the reaction conditions may include a temperature of about 200° C. to about 600° C., e.g., from about 350° C. to about 540° C.; a pressure of from about atmospheric to about 5000 psig, e.g., from about 100 to about 1000 psig; an ethylbenzene feed rate of from about 0.1 WHSV to about 20 WHSV, e.g., from about 2 WHSV to about 10 WHSV; and a hydrogen to ethylbenzene mole ratio of from about 0.1 to about 20, e.g., from about 2 to about 6.

The present catalysts may be used to convert paraffins from high to low molecular weight hydrocarbons in a dewaxing process. Examples of such dewaxing processes are disclosed in U.S. Pat. Nos. 3,700,585; Re. 28,398; 3,968,024; and 4,181,598, the entire disclosures of which are incorporated herein by reference. Hydrocarbon feeds for dewaxing processes include petroleum stocks which have a freeze point or pour point problem, e.g., petroleum stocks boiling above 350° F. Lubricating oil stocks may be feedstocks to a dewaxing process. The dewaxing may be carried out under either cracking or hydrocracking conditions. Cracking conditions for dewaxing may include a liquid hourly space velocity (LHSV) between about 0.5 and 200, a temperature between about 288° C. (550° F.) and 590° C. (1100° F.), a pressure between about subatmospheric and several hundred atmospheres. Hydrocracking conditions for dewaxing may include a liquid hourly space velocity (LHSV) between about 0.1 and 10, a temperature between about 340° C. (650° F.) and 538° C. (1000° F.), a pressure between about 100 and 3000 psig, and a hydrogen to hydrocarbon mole ratio between about one and 20.

The present catalysts may be used to catalyze a variety of alkylaromatic conversion reactions, including isomerization reactions. Such conversions include those described, for example, in U.S. Pat. Nos. 3,856,872; 3,856,873; Re. 30,157; 4,101,595; 4,101,597; 4,312,790; Re. 31,919; and 4,224,141, the entire disclosures of which are incorporated by reference.

As per process conditions described in U.S. Pat. No. 3,856,872 to Morrison, the present catalyst may be used for catalyzing the conversion of $C_8$ aromatics, i.e., xylene and/or ethylbenzene, to para-xylene (octafining) at a temperature of 550° F. (288° C.) to 900° F. (482° C.), a pressure of 150 to 300 psig, and a liquid hourly space velocity (LHSV) of 1 to 200. When used in this reaction, the catalyst may comprise a hydrogenation metal, such as platinum or nickel, and the feed to the reaction may include hydrogen.

As per process conditions described in U.S. Pat. No. 3,856,873 to Burress, the present catalyst may be used for catalyzing the conversion of mixtures of $C_8$ aromatic hydrocarbons to para-xylene in a vapor phase reaction at a temperature of 500° F. (260° C.) to 1000° F. (538° C.), a pressure of 0 (atmospheric) to 1000 psig, and a weight hourly space velocity (WHSV) of 0.5 to 250 with no added hydrogen.

As per process conditions described in U.S. Pat. No. 4,476,330 to Kerr et al., the present catalyst may be used for catalyzing the conversion of aliphatic oxygenates to a higher molecular weight compound at a temperature of 70° F. (21° C.) to 1400° F. (760° C.). The feeds include lower aliphatic organic oxygenates having up to 6 carbon atoms. The oxygenates may be selected from the group consisting of acetals, ketals, acid halides, alcohols, carboxylic acids, aldehydes, acid anhydrides, epoxides, ethers, hemiacetals, gem diols, hydroxy acids, ketones, ketenes, lactones, peracids, peroxides and sugars, especially alcohols, ethers and esters.

The present catalysts may be used as catalysts in the oligomerization of olefins to form gasoline, distillate, lube oils and/or chemicals. Examples of such oligomerization processes are disclosed in U.S. Pat. Nos. 4,517,399; 4,520,221; 4,547,609; and 4,547,613, the entire disclosures of which are incorporated herein by reference.

As per process conditions described in U.S. Pat. No. 4,517,399 to Chester et al., the present catalyst may be used for catalyzing the conversion of olefins having from 3 to 18 carbon atoms, e.g., propylene, to high viscosity, low pour point lubricating oils. Conversion conditions may include a temperature of 350° F. (177° C.) to 650° F. (343° C.), a pressure of 100 to 5000 psig, and a weight hourly space velocity (WHSV) of 0.1 to 10.

The present catalysts may be used as catalysts in the conversion of a variety of aromatic compounds to provide dialkyl-benzene products which are highly enriched in the para-dialkyl substituted benzene isomer. Conversion reactions of this type include aromatics alkylation, transalkylation and disproportionation. Examples of such aromatic alkylation processes are disclosed in U.S. Pat. Nos. 3,755,483; 4,086,287; 4,117,024; and 4,117,026, the entire disclosures of which are incorporated herein by reference.

As per process conditions described in U.S. Pat. No. 3,755,483 to Burress, the present catalyst may be used for catalyzing the alkylation of aromatic hydrocarbons, such as benzene, naphthalene, anthracene and substituted derivatives thereof, e.g., toluene and xylene, with alkylating agents having 1 to 24 carbon atoms under vapor phase conditions. The alkylating agents may be selected from the group consisting of olefins, such as ethylene, propylene and dodecene, aldehydes, such as formaldehyde, alkyl halides and alcohols. Conversion conditions may include an inlet temperature of up to about 900° F. (428° C.), with a reactor bed temperature of up to about 1050° F. (566° C.), a pressure of about atmospheric to about 3000 psig, a ratio of aromatic/alkylating agent of about 1:1 to about 20:1 and a weight hourly space velocity (WHSV) of 20 to 3000.

As per process conditions described in U.S. Pat. No. 4,086,287 to Kaeding et al., the present catalyst may be used for catalyzing the ethylation of toluene or ethylbenzene to produce a para-ethyl derivative, e.g., para-ethyltoluene. Conversion conditions may include a temperature of from about 250° C. to about 600° C., a pressure of 0.1 atmospheres to about 100 atmospheres, a ratio of aromatic/ethylating agent of about 1:1 to about 10:1 and a weight hourly space velocity (WHSV) of 0.1 to 100.

The present catalysts may be used as catalysts in the conversion of light paraffins and olefins to aromatic compounds. Examples of such conversions are disclosed in U.S. Pat. Nos. 3,760,024 and 3,756,942, the entire disclosures of which are incorporated herein by reference.

As per process conditions described in U.S. Pat. No. 3,760,024 to Cattanach, the present catalyst may be used for catalyzing the conversion of paraffins having 2 to 4 carbon atoms and/or olefins to aromatics having from 6 to 10 carbon atoms. The catalyst may, optionally, include a hydrogenation/dehydrogenation component. Conversion conditions may include a temperature of from about 100° C. to about 650° C., a pressure of 0 to about 1000 psig, a ratio of hydrogen/hydrocarbon of about 0 to about 20 and a weight hourly space velocity (WHSV) of 0.1 to 500.

The present catalysts may be used as catalysts in the synthesis of pyridine and substituted pyridines. Process conditions may be selected from those disclosed in U.S. Pat. Nos. 4,675,410 and 4,220,783, the entire disclosures of which are incorporated herein by reference.

The present catalysts may be used as catalysts in the synthesis of caprolactam by the Beckmann rearrangement of cyclohexane oxime. Process conditions may be selected from those disclosed in U.S. Pat. No. 4,359,421, the entire disclosures of which are incorporated herein by reference.

Accordingly, it will be understood that the present catalysts may be used to catalyze a variety of organic, e.g., hydrocarbon, conversion processes. Examples of such processes include cracking hydrocarbons with reaction conditions including a temperature of from about 300°° C. to about 700° C., a pressure of from about 0.1 atmosphere (bar) to about 30 atmospheres and a weight hourly space velocity of from about 0.1 hr$^{-1}$ to about 20 hr$^{-1}$; dehydrogenating hydrocarbon compounds with reaction conditions including a temperature of from about 300° C. to about 700° C., a pressure of from about 0.1 atmosphere to about 10 atmospheres and weight hourly space velocity of from about 0.1 to about 20; converting paraffins to aromatics with reaction conditions including a temperature of from about 300° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g., benzene, toluene and xylene, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g., methanol, or ethers, e.g., dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g., benzene and alkylbenzenes in the presence of an alkylating agent, e.g., olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylkating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

In general, therefore, catalytic conversion conditions over the present catalyst may include a temperature of from about 100° C. to about 760° C., a pressure of from about 0.1 atmosphere (bar) to about 200 atmospheres (bar), a weight hourly space velocity of from about 0.08 hr$^{-1}$ to about 2000 hr$^{-1}$ and a hydrogen/organic, e.g., hydrocarbon compound, of from 0 to about 100.

The present catalyst may, optionally, include a binder material. The optional binder for the present catalyst is preferably an inert, non-alumina containing material, such as silica. However, the binder may also be selected from other materials which may be used exclusively or in combination with one another or with silica. Examples of such binder materials include alumina, zirconia, magnesia, titania, thoria and boria. These materials may be used in the form of dried inorganic oxide gels of gelatinous precipitates. Examples of clay binder materials include bentonite and kieselguhr. The relative proportion of zeolite to the binder material may be about 30 to about 90 percent by weight. The bound catalyst may be in the form of an extrudate, beads or fluidizable microspheres.

Optionally, the present catalyst may contain a hydrogenation/dehydrogenation component. Examples of such optional components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi), and Group VIIB metals (i.e., Mn, Tc and Re). Noble metals (i.e., Pt, Pd, Ir, Rh, Os and Ru) are particular optional hydrogenation/dehydrogenation components. Combinations of catalytic forms of such noble or non-noble metal, such as combinations of Pt with Sn, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction. Preferably, the present catalyst is free of noble metal.

The optional hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetrammineplatinum complexes, platinum chloride, tin sulfate and tin chloride.

The amount of optional hydrogenation/dehydrogenation component may be that amount which imparts or increases the catalytic ability of the overall catalyst to catalytically hydrogenate or dehydrogenate an organic compound under sufficient hydrogenation or dehydrogenation conditions. This amount is referred to herein as a catalytic amount. Quantitatively speaking, when the present catalyst comprises a noble metal, it may comprise, for example, from about 0.001 to about 5 wt%, e.g., from about 0.1 to about 2 wt%, of the noble metal.

EXAMPLE 1

Five grams of ACC4, a 4× selectivated HZSM-5/SiO$_2$, was contacted with 200 ml of a 0.1N solution of NaNO$_3$ (mixture was mixed at room temperature). The exchange was continued for 0.5 hr. The pH of the initial and the zeolite-added solutions is shown below.

| Solution/mixture | pH |
| --- | --- |
| 0.1M NaNO$_3$ solution | 5.8 |
| 0.1M NaNO$_3$ solution + 5 gm ACC4 (after 0.5 hr.) | 3.0 |

The lower pH indicates that Na$^+$ has exchanged into the zeolite while protons are emitted. After washing the 0.5 hr.-exchanged material with 1000 ml of distilled water, the catalyst was dried at 100° C. overnight. Catalytic testing of ACC4 and the exchanged material ACC4# indicated that the exchange procedure reduced the activity of the catalyst.

EXAMPLE 2

Fifty grams of ACC4, a 4× selectivated HZSM-5/SiO$_2$, was contacted with 2 1 of a 0.1N solution of NaNO$_3$ (mixture was mixed at room temperature). The exchange was continued for approximately 18 hrs. The pH of the initial and the zeolite-added solutions is shown below.

| Solution/mixture | pH |
| --- | --- |
| 0.1M NaNO$_3$ solution | 5.8 |
| 0.1M NaNO$_3$ solution + 5 gm ACC4 (after 0.5 hr.) | 2.8 |

Elemental analyses of the sodium-exchanged catalysts suggest that sodium is present at 0.16 wt.%, consistent with the efficacy of the exchange. It is noted that the starting material before sodium exchange contained less than 0.019 wt.% of sodium.

EXAMPLE 3

The base catalyst ACC4 was prepared via multiple selectivation of parent HZSM-5, Si/Al$_2$=26.1, with Dow-550 silicone polymer. A total of four selectivations were carried out, each attempting to add 7.8 wt.% polymer onto the catalyst. The 4× selectivated catalyst was then subjected to exchange with 1M NaNO$_3$ solution. Three exchanges were carried out with a ratio of 50 mL of solution to 1 gram of zeolite extrudate. To illustrate the effectiveness of the exchange, the alpha value decreased from 650 for ACC4 to 36 for the exchanged catalyst. After exchange, the zeolite was dried at ca. 200° C. and used in the catalytic evaluation shown below, wherein ethylbenzene is alkylated with ethylene to selectively produce para-diethylbenzene.

| Conditions | | | | |
| --- | --- | --- | --- | --- |
| Temp, °F. | Feed | 662 | 860 | 896 |
| Pressure, psig | | 100 | 100 | 100 |
| Feed | | | | |
| WHSV (1/H) Ethylbenzene Feed | | 5 | 5 | 5 |
| WHSV (1/H) Ethylene | | 0.376 | 0.376 | 0.376 |
| Ethylbenzene/Ethylene/H$_2$ (molar) | | 4/1/5.1 | 4/1/5.1 | 4/1/5.1 |
| Products | | | | |
| C$_5$— | 7.4 | 4.6 | 4.7 | 5.4 |
| Benzene | | 0.1 | 1.1 | 2.2 |
| Toluene | | 0.1 | 0.2 | 0.2 |
| Ethylbenzene | 92.5 | 94.0 | 88.0 | 85.4 |
| Para-diethylbenzene* | | 1.3 | 5.6 | 6.4 |
| Other | | 0.15 | 0.2 | 0.4 |

*Some baseline trace for meta-diethylbenzene (<1% based on total diethylbenzene isomers)

The above table illustrates that nearly isomerically pure para-diethylbenzene can be produced in this reaction.

EXAMPLE 4

The base catalyst ACC4 was prepared via multiple selectivation of parent HZSM-5, Si/Al$_2$=26.1, with Dow-550 silicone polymer. A total of four selectivations were carried out, each attempting to add 7.8 wt.% polymer onto the catalyst. The 4× selectivated catalyst was then subjected to exchange with 1M NaNO₃ solution. Three exchanges were carried out with a ratio of 50 mL of solution to 1 gram of zeolite extrudate. To illustrate the effectiveness of the exchange, the alpha value decreased from 650 for ACC4 to 36 for the exchanged catalyst. After exchange, the zeolite was dried at ca. 200° C. and used in the catalytic evaluation shown below, wherein toluene is alkylated with ethylene to selectively produce para-ethyltoluene.

| Conditions | | |
|---|---|---|
| Temp, °F. | 842 | 842 |
| Pressure, psig | 100 | 100 |
| Feed | | |
| WHSV (1/H) Toluene Feed | 10 | 5 |
| WHSV (1/H) Ethylene | 0.376 | 0.376 |
| Toluene/Ethylene/H₂ (molar) | 8/1/5.1 | 4/1/5.1 |
| Products | | |
| $C_5-$ | 1.1 | 2.3 |
| Benzene | 0.17 | 0.20 |
| Toluene | 92.09 | 84.55 |
| Ethylbenzene | 0.14 | 0.29 |
| Para-xylene | 0.29 | 0.43 |
| Para-ethyltoluene* | 6.11 | 11.80 |
| Other Heavies | 0.15 | 0.31 |

*Some baseline trace for meta-ethyltoluene (<1% based on total ethyltoluene isomers)

The above table illustrates that nearly isomerically pure para-ethyltoluene can be produced in this reaction.

What is claimed is:

1. A process for disproportionating toluene, said process comprising contacting toluene and hydrogen with a selectivated catalyst under toluene disproportionating conditions, wherein said catalyst is prepared according to the steps of:

(a) contacting a catalyst comprising a zeolite with an organosilicon compound under conditions sufficient to deposit a siliceous material on said catalyst;

(b) contacting the catalyst comprising a zeolite and siliceous material from step (a) with an aqueous solution comprising sodium cations;

(c) washing the aqueous solution treated catalyst from step (b) with water;

(d) drying the washed catalyst from step (c); and (e) recovering a catalyst composition comprising and zeolite, said siliceous material and alkali metal ions from said aqueous solution of step (b).

2. A process for a conversion of an organic compound, said process comprising contacting a reaction stream comprising an organic compound to be converted, under conversion conditions, with a selectivated catalyst prepared according to the steps of:

(a) contacting a catalyst comprising a zeolite with an organosilicon compound under conditions sufficient to deposit a siliceous material on said catalyst;

b) contacting the catalyst comprising a zeolite and siliceous material from step (a) with an aqueous solution comprising at least one alkali metal cation;

(c) washing the aqueous solution treated catalyst from step (b) with water;

(d) drying the washed catalyst from step (c); and (e) recovering a catalyst composition comprising said zeolite, said siliceous material and alkali metal ions from said aqueous solution of step (b); and wherein said organic compound conversion is selected from the group consisting of dewaxing of hydrocarbons, disproportionation of alkylaromatics, isomerization of alkylaromatics, oligomerization of olefins, transalkylation of aromatics, conversion of oxygenates to hydrocarbons, rearrangement of oxygenates, and conversion of paraffins and olefins to aromatics.

3. A process according to claim 2, wherein the conversion conditions comprise a temperature of from about 100° C. to about 760° C., a pressure of about 0.1 atmosphere to about 200 atmospheres, a weight hourly space velocity of from about 0.08 $hr^{-1}$ to about 2000 $hr^{-1}$, and a hydrogen/hydrocarbon molar ratio of from about 0 to about 100.

* * * * *